(12) United States Patent
Yang et al.

(10) Patent No.: US 9,265,477 B2
(45) Date of Patent: Feb. 23, 2016

(54) ADAPTIVE LIGHTWEIGHT ACOUSTIC SIGNAL CLASSIFICATION FOR PHYSIOLOGICAL MONITORING

(75) Inventors: Te-Chung Isaac Yang, Aliso Viejo, CA (US); Yongji Fu, Vancouver, WA (US)

(73) Assignee: Sharp Laboratories of America, Inc., Camas, WA (US)

(*) Notice: Subject to any disclaimer, the term of this patent is extended or adjusted under 35 U.S.C. 154(b) by 1273 days.

(21) Appl. No.: 12/932,130

(22) Filed: Feb. 17, 2011

(65) Prior Publication Data

US 2012/0215454 A1     Aug. 23, 2012

(51) Int. Cl.
| | |
|---|---|
| *A61B 7/00* | (2006.01) |
| *G01N 29/14* | (2006.01) |
| *A61B 5/00* | (2006.01) |
| *G06K 9/00* | (2006.01) |
| *A61B 5/024* | (2006.01) |
| *A61B 5/08* | (2006.01) |

(52) U.S. Cl.
CPC ............... *A61B 7/00* (2013.01); *A61B 5/7235* (2013.01); *G01N 29/14* (2013.01); *G06K 9/00536* (2013.01); *A61B 5/024* (2013.01); *A61B 5/0816* (2013.01); *G01N 2291/02483* (2013.01)

(58) Field of Classification Search
CPC ........ A61B 7/00; A61B 7/003; A61B 5/7235; A61B 5/024; A61B 5/0816; A61B 5/08; G06K 9/00536; G01N 29/14; G01N 2291/02483
USPC ........................... 702/189; 600/529, 538, 484
See application file for complete search history.

(56) References Cited

U.S. PATENT DOCUMENTS

| | | | |
|---|---|---|---|
| 5,143,078 A | 9/1992 | Mather et al. | |
| 6,974,414 B2 | 12/2005 | Victor | 600/300 |
| 7,505,901 B2 | 3/2009 | Kaltenmeier et al. | 704/231 |
| 2007/0282174 A1* | 12/2007 | Sabatino | 600/300 |
| 2008/0161707 A1* | 7/2008 | Farringdon et al. | 600/509 |
| 2008/0300867 A1 | 12/2008 | Yan | 704/207 |
| 2010/0262031 A1 | 10/2010 | Fu et al. | |

FOREIGN PATENT DOCUMENTS

| | | | |
|---|---|---|---|
| EP | 1770545 | 4/2007 | ............. G06F 17/00 |
| WO | WO99/60169 | 11/1999 | |

OTHER PUBLICATIONS

Shoichi Matsunaga et al., "Classification Between Normal and Abnormal Respiratory Sounds Based on Maximum Likelihood Approach," Proc. IEEE Int. Conf. Acoust. Speech Signal Process., 2009, vol. 1, pp. 517-520.

\* cited by examiner

*Primary Examiner* — Manuel L Barbee
(74) *Attorney, Agent, or Firm* — Scot A. Reader

(57) ABSTRACT

The present invention provides adaptive lightweight acoustic signal classification for physiological monitoring applications. In an exemplary implementation, the total energy of a segment of an acoustic signal recording body sounds is first determined. For each of a plurality of signal classes (e.g., good, noisy, weak), the probability that the segment belongs to the signal class is then calculated using the total energy and profile data for the signal class. The segment is then assigned to one of the plurality of signal classes by reference to the probabilities. Physiological data are then selectively generated and outputted using the segment, depending on the assigned signal class, and the segment is selectively applied as feedback to update profile data for the assigned signal class.

19 Claims, 5 Drawing Sheets

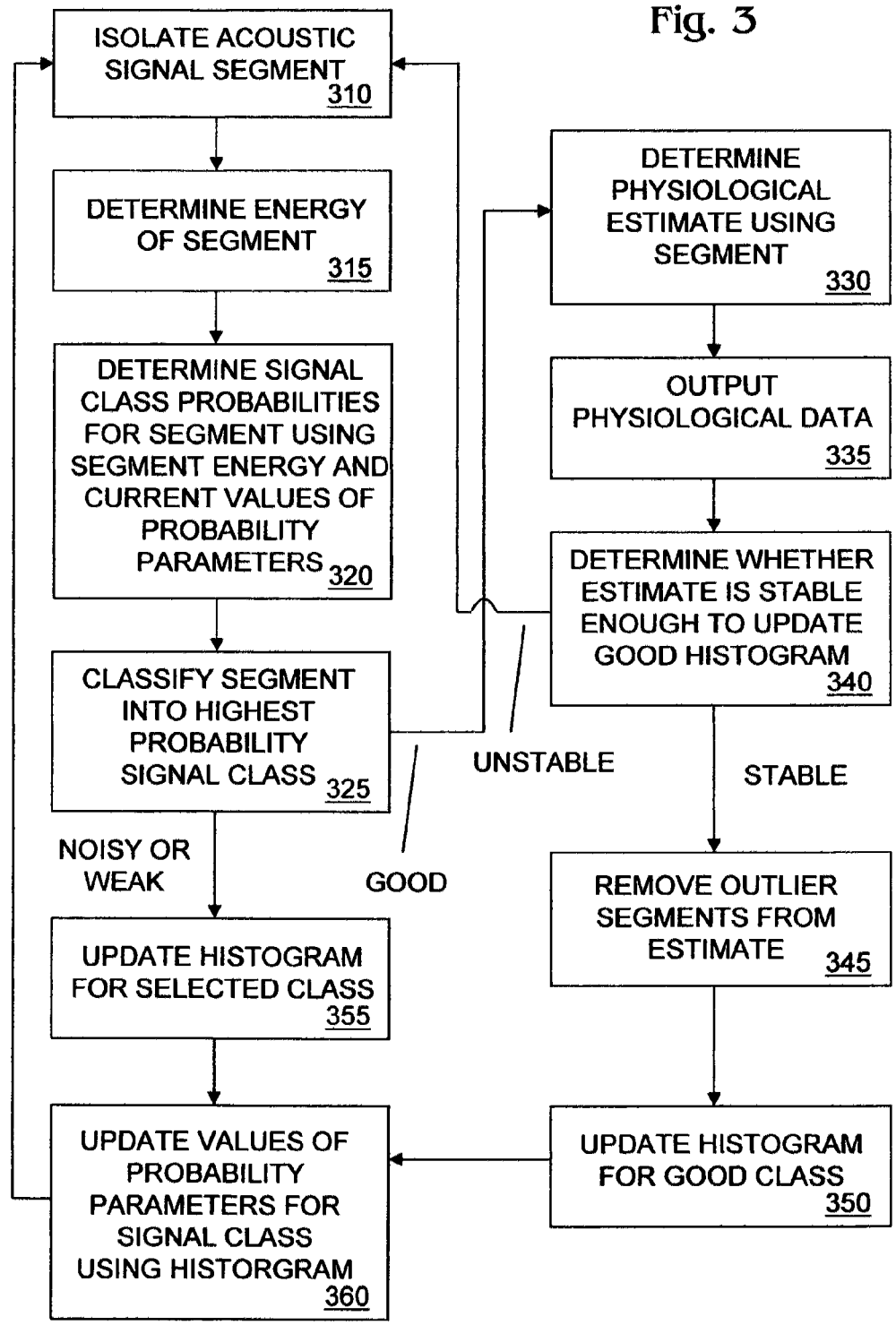

ADAPTIVE LIGHTWEIGHT ACOUSTIC SIGNAL CLASSIFICATION FOR PHYSIOLOGICAL MONITORING

BACKGROUND OF THE INVENTION

The present invention relates to physiological monitoring and, more particularly, acoustic signal classification in physiological monitoring.

Physiological monitoring is in widespread use managing chronic diseases and in elder care. Physiological monitoring is often performed using wearable devices that acquire and analyze acoustic signals that contain heart and lung sounds as people go about their daily lives. However, such acoustic signals are not always reliable. For example, an acoustic signal may be too noisy to reliably detect heart or lung sounds if taken when a person speaks, or is in motion, or is in an environment with high background noise. Moreover, an acoustic signal may be too weak to reliably detect heart or lung sounds if taken when an acoustic sensor of the monitoring device is not placed at the proper body location or when an air chamber of the acoustic sensor is not fully sealed. When an acoustic signal is too noisy or too weak, confidence in physiological data extracted from the signal, such as the patient's heart or respiration rate, may be very low.

Reliance on physiological data extracted from an unreliable acoustic signal can have serious adverse consequences on patient health. For example, such physiological data can lead a patient or his or her clinician to improperly interpret the patient's physiological state and cause the patient to undergo treatment that is not medically indicated or forego treatment that is medically indicated.

Various methods and systems have been proposed to classify acoustic signals to distinguish between reliable and unreliable signals and "weed out" unreliable signals for purposes of physiological monitoring. However, such classification schemes have generally been non-adaptive and unduly complex.

SUMMARY OF THE INVENTION

The present invention provides adaptive lightweight acoustic signal classification for physiological monitoring applications. In an exemplary implementation, the total energy of a segment of an acoustic signal recording body sounds is first determined. For each of a plurality of signal classes (e.g., good, noisy, weak), the probability that the segment belongs to the signal class is then calculated using the total energy and profile data for the signal class. The segment is then assigned to one of the plurality of signal classes by reference to the probabilities. Physiological data are then selectively generated and outputted using the segment, depending on the assigned signal class, and the segment is selectively applied as feedback to update profile data for the assigned signal class.

In one aspect of the invention, a physiological monitoring device comprises an sound capture system adapted to generate an acoustic signal recording body sounds, an acoustic signal processing system operatively coupled with the capture system and adapted to determine a total energy of a segment of the signal, calculate for each of a plurality of signal classes a probability that the segment belongs to the signal class based at least in part on the total energy and profile data for the signal class, and assign the segment to one of the plurality of signal classes based at least in part on the probabilities, and a physiological data output system operatively coupled with the processing system and adapted to selectively output, depending on the assigned signal class, physiological data based at least in part on the segment.

In some embodiments, the processing system is further adapted to selectively update profile data for the assigned signal class based at least in part on the segment.

In some embodiments, the processing system assigns the segment to the signal class associated with the highest probability.

In some embodiments, the profile data for each of the plurality of signal classes comprise histogram data containing a probability distribution of segments assigned to the signal class as a function of total energy.

In some embodiments, the profile data for each of the plurality of signal classes comprise a mean total energy of segments assigned to the signal class and a total energy variance of segments assigned to the signal class.

In some embodiments, the plurality of signal classes comprise a good class, a noisy class and a weak class.

In some embodiments, in response to assigning the segment to a good class, the processing system determines whether the segment is an outlier and selectively updates, depending on whether the segment is an outlier, profile data for the good class. In some embodiments, determining whether the segment is an outlier comprises determining whether the total energy of the segment is within a predetermined number of standard deviations of a mean total energy of segments assigned to the good class. In some embodiments, determining whether the segment is an outlier comprises determining whether the total energy of the segment exceeds a saturation threshold.

In some embodiments, in response to assigning the segment to a noisy class, the processing system updates profile data for the noisy class.

In some embodiments, in response to assigning the segment to a weak class, the processing system updates profile data for the weak class.

In some embodiments, in response to assigning the segment to a good class, the output system outputs physiological data based at least in part on the segment.

In some embodiments, in response to assigning the segment to a noisy class, outputting of physiological data based at least in part on the segment is inhibited.

In some embodiments, in response to assigning the segment to a weak class, outputting of physiological data based at least in part on the segment is inhibited.

In another aspect of the invention, an acoustic signal processing method for a physiological monitoring device comprises the steps of generating by the device an acoustic signal recording body sounds; determining by the device a total energy of a segment of the signal; calculating by the device, for each of a plurality of signal classes, a probability that the segment belongs to the signal class based at least in part on the total energy and profile data for the signal class; assigning by the device the segment to one of the plurality of signal classes based at least in part on the probabilities; and selectively outputting by the device, depending on the assigned signal class, physiological data based at least in part on the segment.

In some embodiments, the method further comprises the step of selectively updating by the device profile data for the assigned signal class based at least in part on the segment.

In yet another aspect of the invention, an acoustic signal processing method comprises the steps of receiving by an acoustic signal processing system an acoustic signal recording body sounds; determining by the system a total energy of a segment of the signal; calculating by the system, for each of a plurality of signal classes, a probability that the segment belongs to the signal class based at least in part on the total energy and profile data for the signal class; assigning by the system the segment to one of the plurality of signal classes based at least in part on the probabilities; and selectively outputting by the system, depending on the assigned signal class, physiological parameter information based at least in part on the segment.

In some embodiments, the method further comprises the step of selectively updating by the system profile data for the assigned signal class based at least in part on the segment.

These and other aspects of the invention will be better understood by reference to the following detailed description taken in conjunction with the drawings that are briefly described below. Of course, the invention is defined by the appended claims.

BRIEF DESCRIPTION OF THE DRAWINGS

FIG. 3 shows an adaptive lightweight acoustic signal classification method for a physiological monitoring device in some embodiments of the invention.

DETAILED DESCRIPTION OF A PREFERRED EMBODIMENT

Figure 1:
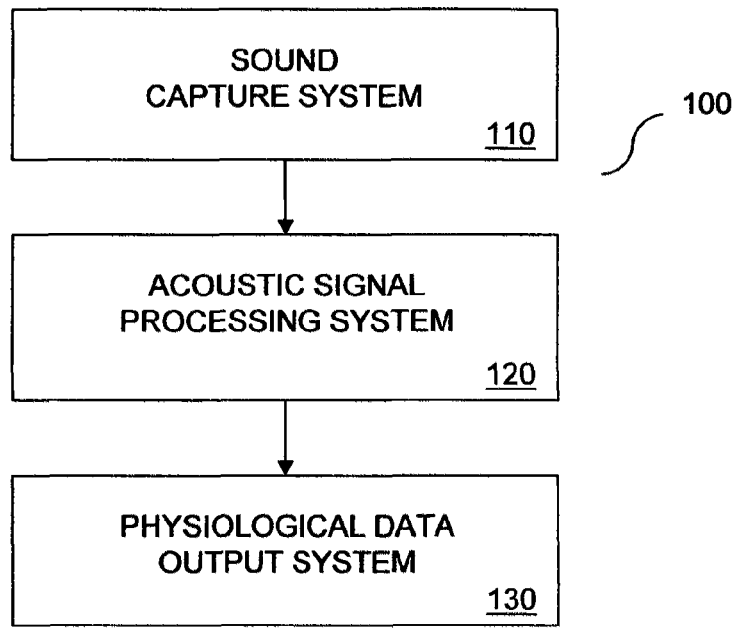
FIG. 1 shows a physiological monitoring device in some embodiments of the invention.

FIG. 1 shows a physiological monitoring device 100 in some embodiments of the invention. Monitoring device 100 includes a sound capture system 110, an acoustic signal processing system 120 and a physiological data output system 130, which are communicatively coupled in series.

Capture system 110 continually detects body sounds, such as heart and lung sounds, at a detection point, such as a trachea, chest or back of a person being monitored, and continually transmits an acoustic signal recording the detected body sounds to processing system 120. Capture system 110 may include, for example, a sound transducer positioned on the body of a human subject that detects body sounds, as well as amplifiers, filters, an analog/digital (A/D) converter and/or automatic gain control (AGC) that generate an acoustic signal embodying the detected body sounds.

Processing system 120, under control of a processor executing software instructions, continually processes the acoustic signal and generates estimates of one or more physiological parameters for the subject being monitored. Monitored physiological parameters may include, for example, heart rate and respiration rate. To enable reliable estimation of physiological parameters, processing system 120 isolates and evaluates continual, non-overlapping segments of the acoustic signal and classifies the segments into good, noisy and weak signal classes, wherein only those segments classified as good are used to generate physiological parameter estimates. By way of example, each segment may include 100 samples taken at a sampling rate of 3.2 KHz, resulting in each segment having a length of 1/32 seconds. Processing system 120 transmits to output system 130 for outputting information relative to recently generated physiological parameter estimates. In some embodiments, processing system 120 may perform processing functions described herein in custom logic rather than software, or in a combination of software and custom logic.

In some embodiments, output system 130 has a display screen for displaying physiological data determined using physiological parameter estimates received from processing system 120. In some embodiments, output system 130 in lieu of or in addition to a display screen has an interface to an internal or external data management system that stores physiological data determined using physiological parameter estimates received from processing system 120, and/or an interface that transmits physiological data determined using physiological parameter estimates received from processing system 120 to a remote monitoring device, such as a monitoring device at a clinician facility. Physiological data outputted by output system 130 may include the physiological parameter estimates received from processing system 120 and/or physiological data derived from such physiological parameter estimates.

In some embodiments, capture system 110, processing system 120 and output system 130 are part of a portable ambulatory monitoring device that monitors a person's physiological well-being in real-time as the person performs daily activities. In other embodiments, capture system 110, processing system 120 and output system 130 may be part of separate devices that are remotely coupled via wired or wireless data communication links.

Figure 2:
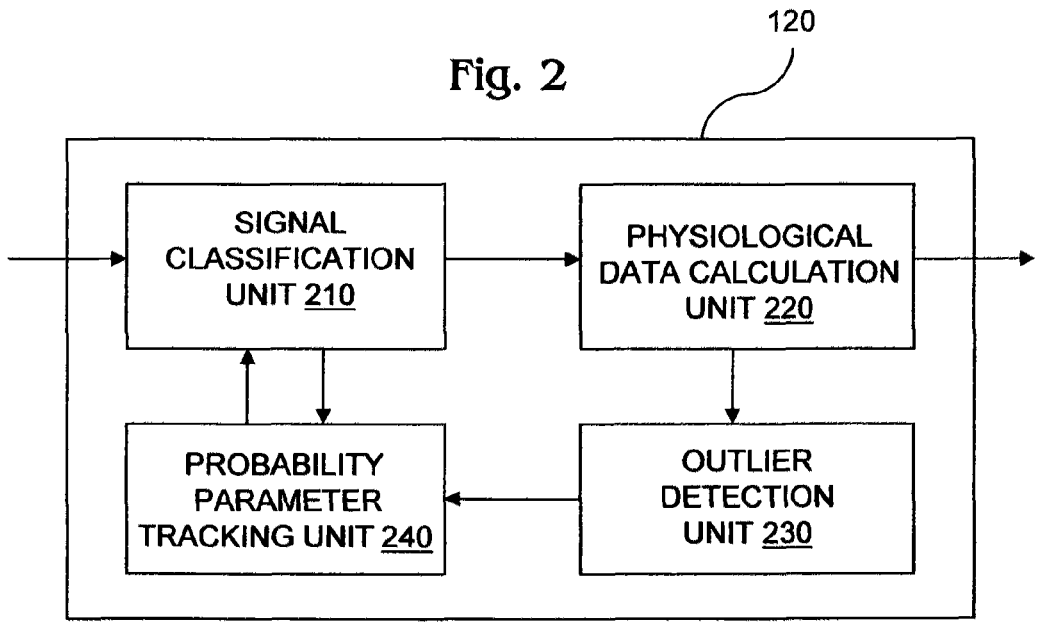
FIG. 2 shows the acoustic signal processing system of the physiological monitoring device of FIG. 1.

FIG. 2 shows processing system 120 to include a signal classification unit 210, a physiological data calculation unit 220, an outlier detection unit 230 and a probability parameter tracking unit 240, which are communicatively coupled in a closed feedback loop. Classification unit 210 and detection unit 230 also have direct access to tracking unit 240. As described in FIG. 3 in some embodiments, units 210, 220, 230, 240, under processor control, interact to deliver an adaptive lightweight acoustic signal classification capability that operates on segments of an acoustic signal received by classification unit 210 from capture system 110.

Turning now to FIG. 3, in runtime operation, classification unit 210 continually receives an acoustic signal from capture system 110 and isolates the next acoustic signal segment (310), which in some embodiments includes 100 samples taken at 3.2 KHz (i.e., a segment having a length of 1/32 seconds).

Next, classification unit 210 determines the total energy of the segment according to the formula $$E_n = \sum_{k=1}^{100} data_k^2$$

where $E_n$ is the total energy of the 100 samples $data_k$ in the segment (315). Next, classification unit 210 calculates, for each of three signal classes (good, noisy and weak), a probability that the segment belongs to the signal class based using the total energy of the segment and profile data for the signal class (320). The probabilities are calculated according to the offset Rayleigh distribution $$P(x; \sigma, x_0) = \begin{cases} \left(\frac{x-x_0}{\sigma^2}\right)e^{\frac{-(x-x_0)^2}{2\sigma^2}}, & x \geq x_0 \\ 0, & x < x_0 \end{cases}$$

where $P(x; \sigma, x_0)$ is the probability that the segment belongs to the signal class, x equals the segment's total energy $E_n$, $\sigma$ is the Rayleigh distribution parameter for the signal class and $x_0$ is a translation parameter for the probability distribution of histogram data for the signal class. The Rayleigh distribution parameter $\sigma$ may be determined from curve-fitting histogram data for the signal class or may be computed directly using the formula $$\sigma = \sqrt{\frac{2v}{4-\pi}}$$

where v is the variance in the histogram data for the signal class. Similarly, the translation parameter $x_0$ may be determined from curve-fitting histogram data for the signal class or may be computed directly using the formula $$\mu = \sqrt{\frac{\pi}{2}}\sigma + x_0$$

where $\mu$ is the mean total energy of segments in the histogram data for the signal class. The histogram data for each signal class is stored on tracking unit 240 and contains a probability distribution of previous segments assigned to the signal class as a function of total energy. In some embodiments, classification unit 210 retrieves the histogram data from tracking unit 240 and determines the probability parameters (e.g., $\sigma$, $x_0$, mean, variance) for each signal class from the retrieved histogram data. In other embodiments, tracking unit 240 determines the probability parameters for each signal class from the histogram data and classification unit 210 accesses these pre-computed probability parameters from tracking unit 240.

Figure 4A:
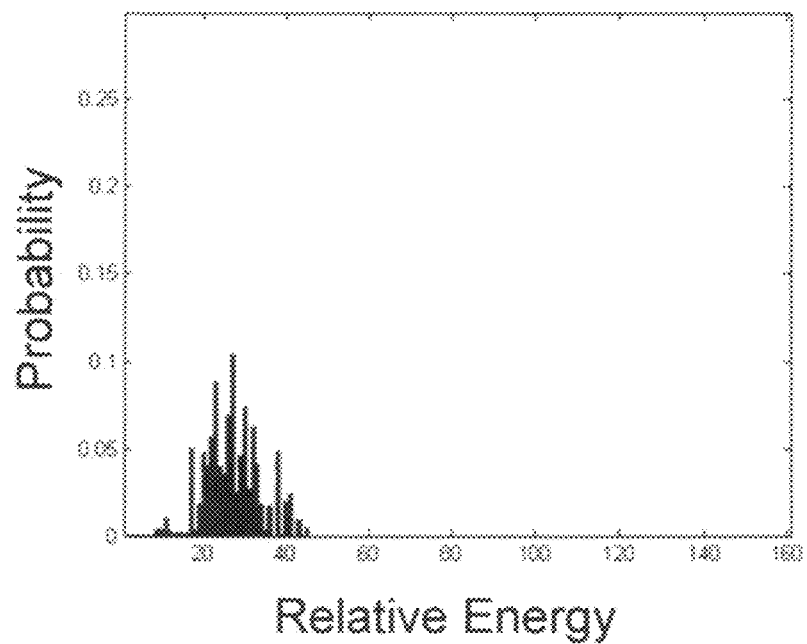
FIGS. 4A and 4B show exemplary energy/probability histograms for signal segments classified as good at a first and second time, respectively.

Exemplary histograms for good, noisy and weak signal classes are shown in FIGS. 4-6. Turning first to FIG. 4A, an exemplary histogram for the good signal class at a time T shows that segments assigned to the good signal class have relative energies concentrated between 20 and 40, with the distribution decaying more slowly on the right side of the peak than on the left side.

Figure 4B:
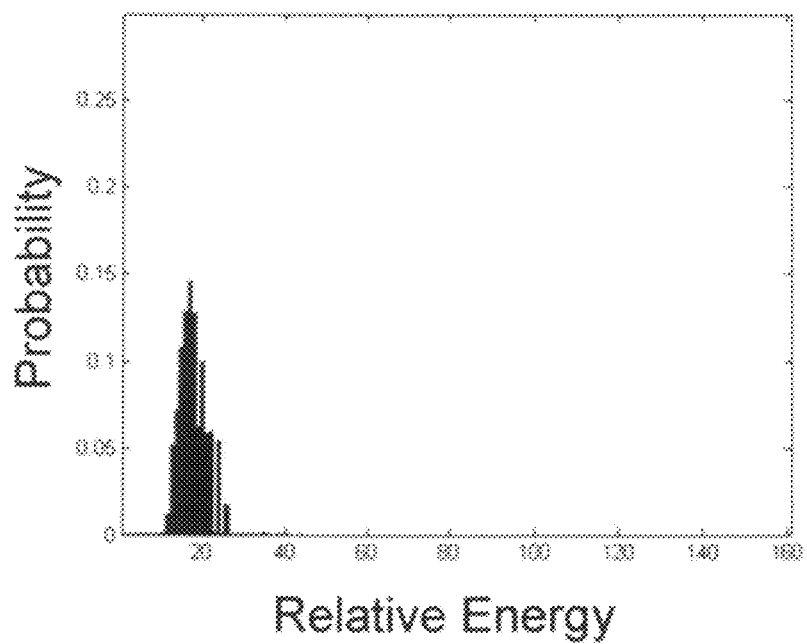

Turning next to FIG. 4B, an exemplary histogram for the good signal class at a later time T+t shows that segments assigned to the good signal class have relative energies concentrated between 10 and 30, with the distribution still decaying more slowly on the right side of the peak than on the left side. Relative to the earlier histogram, the later histogram exhibits drift to the left due to replacement of older, higher relative energy segments with newer, lower relative energy segments.

Figure 5A:
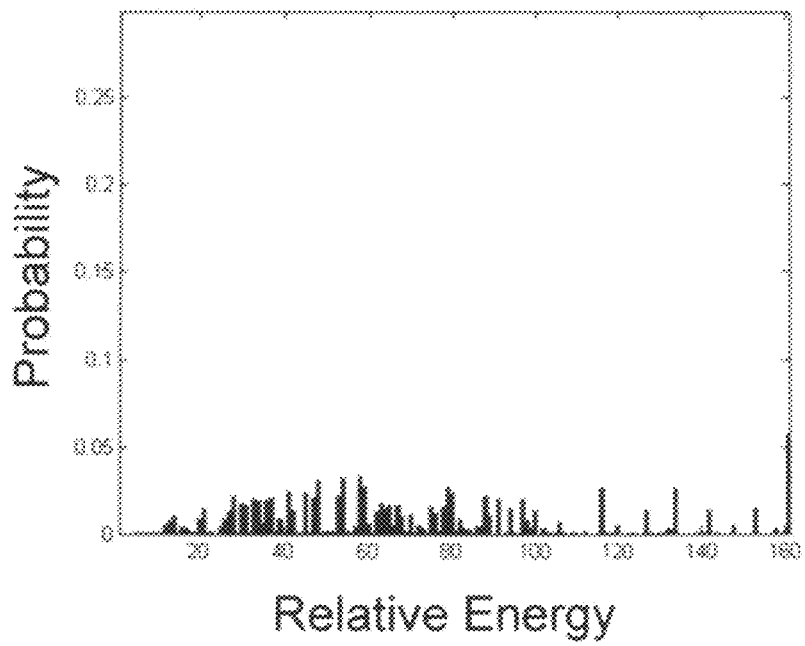
FIGS. 5A and 5B show exemplary energy/probability histograms for signal segments classified as noisy at a first and second time, respectively.

Turning next to FIG. 5A, an exemplary histogram for the noisy signal class at a time T shows that segments assigned to the noisy signal class have relative energies spread fairly evenly throughout the spectrum. The concentration of segments at the maximum relative energy of the histogram (e.g., 160) reflects the plotting of segments that have relative energies higher than the maximum limit of the histogram at the maximum limit to ensure that these high energy segments are represented on the histogram.

Figure 5B:
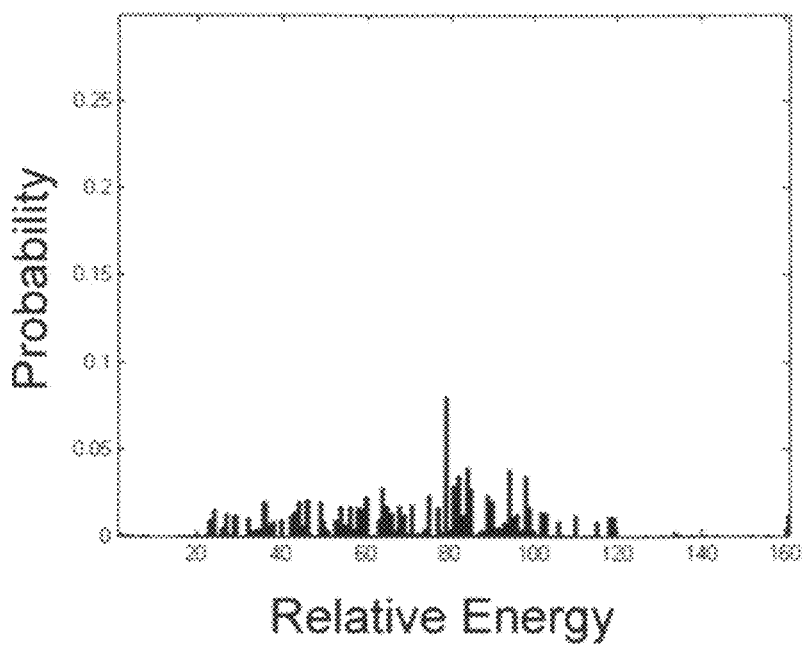

Turning next to FIG. 5B, an exemplary histogram for the noisy signal class at a later time T+t shows that segments assigned to the noisy signal class have relative energies that remain spread fairly evenly throughout the spectrum, although the distribution in the later histogram is somewhat more concentrated near the middle of the plotted range.

Figure 6A:
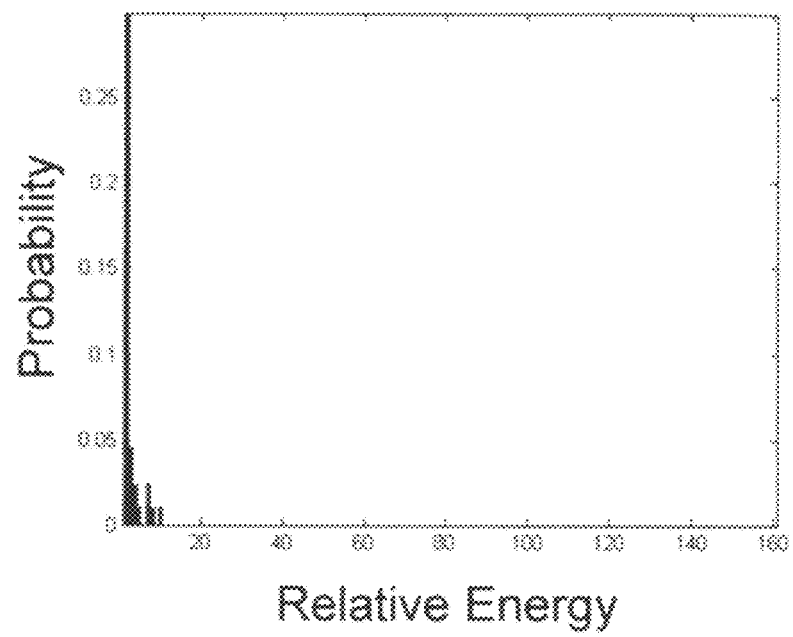
FIGS. 6A and 6B show exemplary energy/probability histograms for signal segments classified as weak at a first and second time, respectively.

Turning next to FIG. 6A, an exemplary histogram for the weak signal class at a time T shows that segments assigned to the weak signal class have relative energies concentrated at near zero energy, with the distribution decaying rapidly toward a relative energy of 10.

Figure 6B:
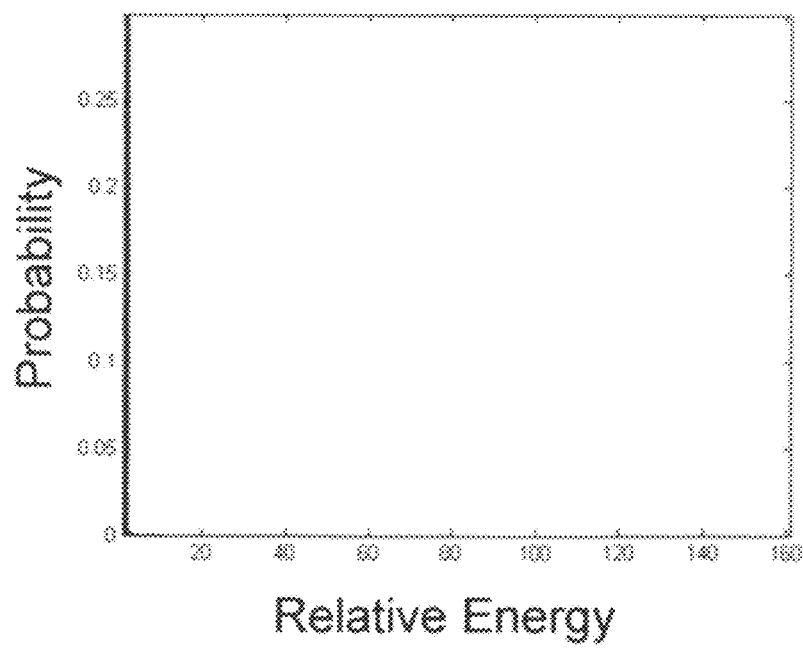

Turning finally to FIG. 6B, an exemplary histogram for the weak signal class at a later time T+t shows that an even greater concentration of segments assigned to the good signal class with relative energies near zero energy.

Returning now to FIG. 3, the method flow proceeds with classification unit 210 classifying the segment into the signal class associated with the highest calculated probability (325). That is, the probabilities calculated for each signal class (e.g., good, noisy, weak) using the segment's total energy and profile data for the signal class (e.g., histogram data, $\sigma$, $x_0$, mean, variance) are compared, and the segment is classified into the signal class to which the segment is considered most likely to belong based on these probabilities.

The method flow then continues down one of two paths depending on whether the segment has been classified into the good class, indicating that the segment is sufficiently reliable to use in estimating physiological parameters, or into the noisy or weak class, indicating that the segment is insufficiently reliable to use in estimating physiological parameters. With regard to the two unreliable classes, noisy segments have a signal-to-noise ratio that is too low to permit extraction of reliable physiological data and weak segments have signals that are too weak to permit extraction of reliable physiological data. Accordingly, segments classified as noisy and weak are excluded from use in physiological parameter estimation.

If the segment is classified as good, classification unit 210 transmits the segment to calculation unit 220, which applies the segment in generating an estimate of one or more physiological parameters, such as heart rate or respiratory rate (330). In some embodiments, calculation unit 220 combines the segment with neighboring segments of the acoustic signal that are classified as good and generates the physiological parameter estimate using the combined segments.

Next, calculation unit 220 transmits the estimate to output system 130, which outputs physiological data that may include the estimate itself and/or physiological data derived from the estimate (335).

Calculation unit 220 also determines whether the estimate is sufficiently stable to be used to update the histogram for the good signal class (340). For example, calculation unit 220 may examine whether the combined segments used in generating the estimate exhibit a variance that is too large to consider the estimate stable. If calculation unit 220 determines that the estimate is not stable enough, the method flow returns to Step 310 and the next segment is processed without updating the histogram for the good signal class. Otherwise, calculation unit 220 transmits the combined segments to detection unit 230 for further processing and eventual updating of the histogram for the good signal class.

Next, detection unit 230 removes outlier segments from the estimate to prevent incipient divergence in the closed feedback loop (345). Detection unit 230 determines whether any segment included in the estimate has a total energy more than three standard deviations above the mean total energy for the good signal class. Detection unit 230 accesses tracking unit 240 to obtain the mean total energy and standard deviation for the good signal class. Detection unit 230 also determines whether any segment included in the estimate has a total energy that exceeds a saturation threshold. Detection unit 230 removes any segment that meets either of these two outlier conditions from the estimate, and transmits the remaining segments to tracking unit 240.

Next, tracking unit 240 updates the histogram for the good signal class using the remaining segments from the estimate (350). If the histogram is not yet fully populated, the remaining segments from the estimate are simply added to the histogram data. If the histogram is already fully populated, the remaining segments from the estimate replace the oldest segments in the histogram so as to keep the histogram populated with the most recent data.

Finally, the probability parameters (e.g., $\sigma$, $x_0$, mean, variance) for the good signal class are updated using the updated histogram data (360). This operation may be performed by tracking unit 240, or by classification unit 210 after being notified by tracking unit 240 of the update and retrieving the updated histogram data from tracking unit 240. The flow then returns to Step 310 and the next segment is classified by reference to the updated probability parameters.

If the segment is classified as noisy or weak in Step 325, classification unit 210 transmits the segment directly to tracking unit 240, which updates the histogram for either the noisy or weak signal class, as appropriate, using the segment (355). If the histogram is not yet fully populated, the segment is simply added to the histogram data. If the histogram is already fully populated, the segment replaces the oldest segment in the histogram so as to keep the histogram populated with the most recent data. The probability parameters (e.g., $\sigma$, $x_0$, mean, variance) for the noisy or weak signal class are then updated using the updated histogram data (360) either by tracking unit 240 or by classification unit 210. The flow then returns to Step 310 and the next segment is classified using the updated probability parameters.

Naturally, when device 100 boots-up, the runtime histograms for the good, noisy and weak signal classes are not yet populated. Accordingly, tracking unit 240 maintains default histograms populated with data that are considered representative of the those signal classes, or maintains default values of the Rayleigh distribution parameter $\sigma$ and the translation parameter $x_0$ for those signal classes. The default histograms or values, which may be factory or user configured, are used by device 100 until the runtime histograms become fully populated.

Moreover, in some embodiments, the Rayleigh distribution parameter $\sigma$ and the translation parameter $x_0$ for the weak signal class are non-updateable. In these embodiments, no histogram is required to be maintained for the weak signal class and no histogram updates are performed for the weak signal class.

It will be appreciated by those of ordinary skill in the art that the invention can be embodied in other specific forms without departing from the spirit or essential character hereof. The present description is thus considered in all respects to be illustrative and not restrictive. The scope of the invention is indicated by the appended claims, and all changes that come with in the meaning and range of equivalents thereof are intended to be embraced therein.

What is claimed is:

1. A physiological monitoring device, comprising:
a sound capture system adapted to detect body sounds and generate an acoustic signal representing the body sounds, the sound capture system including a sound transducer positioned on a body, an amplifier, a filter, an analog-to-digital converter and automatic gain control;
an acoustic signal processing system operatively coupled with the capture system and adapted to determine a total energy of a segment of the signal, calculate for each of a plurality of signal classes a probability that the segment belongs to the signal class based at least in part on the total energy and profile data for the signal class, and assign the segment to one of the plurality of signal classes based at least in part on the probabilities; and
a physiological data output system operatively coupled with the processing system and adapted to selectively output, depending on the assigned signal class, physiological data based at least in part on the segment, wherein in response to assigning the segment to a good class, the output system outputs physiological data based at least in part on the segment.

2. The device of claim 1, wherein the processing system is further adapted to selectively update profile data for the assigned signal class based at least in part on the segment.

3. The device of claim 1, wherein the processing system assigns the segment to the signal class associated with the highest probability.

4. The device of claim 1, wherein the profile data for each of the plurality of signal classes comprise histogram data containing a probability distribution of segments assigned to the signal class as a function of total energy.

5. The device of claim 1, wherein the profile data for each of the plurality of signal classes comprise a mean total energy of segments assigned to the signal class and a total energy variance of segments assigned to the signal class.

6. The device of claim 1, wherein the plurality of signal classes comprise a good class, a noisy class and a weak class.

7. The device of claim 1, wherein in response to assigning the segment to a good class, the processing system determines whether the segment is an outlier and selectively updates, depending on whether the segment is an outlier, profile data for the good class.

8. The device of claim 7, wherein the processing system determines whether the segment is an outlier at least in part by determining whether the total energy of the segment is within a predetermined number of standard deviations of a mean total energy of segments assigned to the good class.

9. The device of claim 7, wherein the processing system determines whether the segment is an outlier at least in part by determining whether the total energy of the segment exceeds a saturation threshold.

10. The device of claim 1, wherein in response to assigning the segment to a noisy class, the processing system updates profile data for the noisy class.

11. The device of claim 1, wherein in response to assigning the segment to a weak class, the processing system updates profile data for the weak class.

12. The device of claim 1, wherein in response to assigning the segment to a noisy class, outputting of physiological data based at least in part on the segment is inhibited.

13. The device of claim 1, wherein in response to assigning the segment to a weak class, outputting of physiological data based at least in part on the segment is inhibited.

14. An acoustic signal processing method for a physiological monitoring device, comprising the steps of:
detecting by the device body sounds;
generating by the device an acoustic signal representing the body sounds, wherein the detecting and generating steps are performed using a sound capture system, the sound capture system including a sound transducer positioned on a body, an amplifier, a filter, an analog-to-digital converter and automatic gain control;

determining by the device a total energy of a segment of the signal;

calculating by the device, for each of a plurality of signal classes, a probability that the segment belongs to the signal class based at least in part on the total energy and profile data for the signal class;

assigning by the device the segment to one of the plurality of signal classes based at least in part on the probabilities; and selectively outputting by the device, depending on the assigned signal class, physiological data based at least in part on the segment, wherein in response to assigning the segment to a good class, the device outputs physiological data based at least in part on the segment.

15. The method of claim 14, further comprising the step of selectively updating by the device profile data for the assigned signal class based at least in part on the segment.

16. The method of claim 14, wherein the profile data for each of the plurality of signal classes comprise histogram data containing a probability distribution of segments assigned to the signal class as a function of total energy.

17. The method of claim 14, wherein the profile data for each of the plurality of signal classes comprise a mean total energy of segments assigned to the signal class and a total energy variance of segments assigned to the signal class.

18. An acoustic signal processing method, comprising the steps of:

detecting by a sound capture system body sounds;

generating by the sound capture system an acoustic signal representing the body sounds, wherein the sound capture system includes a sound transducer positioned on a body, an amplifier, a filter, an analog-to-digital converter and automatic gain control;

receiving by an acoustic signal processing system the signal;

determining by the processing system a total energy of a segment of the signal;

calculating by the processing system, for each of a plurality of signal classes, a probability that the segment belongs to the signal class based at least in part on the total energy and profile data for the signal class;

assigning by the processing system the segment to one of the plurality of signal classes based at least in part on the probabilities; and selectively outputting by the processing system, depending on the assigned signal class, physiological parameter information based at least in part on the segment, wherein in response to assigning the segment to a good class, the processing system outputs physiological parameter information based at least in part on the segment.

19. The method of claim 18, further comprising the step of selectively updating by the processing system profile data for the assigned signal class based at least in part on the segment.

* * * * *